United States Patent [19]

Eskelinen

[11] Patent Number: 4,892,621

[45] Date of Patent: Jan. 9, 1990

[54] METHOD AND DEVICE FOR MEASURING PERMEABILITY/PENETRABILITY OF FABRIC IN A PAPER MACHINE

[75] Inventor: Pekka Eskelinen, Karhula, Finland

[73] Assignee: Valmet Paper Machinery, Inc., Finland

[21] Appl. No.: 249,358

[22] Filed: Sep. 23, 1988

[30] Foreign Application Priority Data

Sep. 23, 1987 [FI] Finland ............................ 874161

[51] Int. Cl.$^4$ .................. D21F 7/00; G01N 15/08
[52] U.S. Cl. ............................ 162/198; 162/263; 162/274; 73/37.7; 73/38
[58] Field of Search ................ 162/198, 263, 274; 73/38, 37.7

[56] References Cited

U.S. PATENT DOCUMENTS 3,371,518  3/1968  Keyes ................................ 73/38
4,495,796  1/1985  Hester et al. ...................... 73/37.7

Primary Examiner—Richard V. Fisher
Assistant Examiner—Christopher Upton
Attorney, Agent, or Firm—Steinberg & Raskin

[57] ABSTRACT

The present invention concerns a method in a paper machine for the measurement of air penetrability or permeability of fabrics penetrable by air, in particular of a wire or felt. In the method, the fabric penetrable by air such as a wire is passed over at least one roll, where a positive pressure is formed at an inlet side of the fabric with respect to the roll when the fabric runs and in an inlet nip formed between the moving fabric and a face of the roll, and a negative pressure is formed at an outlet side of the moving fabric with respect to the roll in an outlet nip formed between the moving fabric and the roll face. The positive pressure and negative pressure depend up on the permeability of the fabric penetrable by air. According to the method, at least one device is mounted below the fabric penetrable by air such as a wire, this device being sealed relative to the moving roll face so that an at least partially closed pressure space is formed between the device, the roll face, and the fabric. While the fabric penetrable by air such as the wire moves, the pressure is measured out of the pressure space and the permeability of the fabric penetrable by air is calculated from the measured pressure value. The present invention also concerns a device for carrying out this method.

20 Claims, 3 Drawing Sheets

METHOD AND DEVICE FOR MEASURING PERMEABILITY/PENETRABILITY OF FABRIC IN A PAPER MACHINE

BACKGROUND OF THE INVENTION

The present invention concerns a method in a paper machine for the measurement of the air penetrability or permeability of fabrics penetrable by air, in particular of a wire or felt, in which the fabric penetrable by air such as the wire is passed over at least one roll where a positive pressure is formed when the fabric runs at the inlet side of the fabric or roll in an inlet nip formed between the moving fabric and a face of the roll, and a negative pressure is formed at an outlet side of the moving fabric or roll in an outlet nip formed between the fabric and the roll face, these positive and negative pressures depending upon the permeability of the fabric penetrable by air.

The present invention also concerns a device in a paper machine intended for carrying out the method for measuring the air penetrability or permeability of fabrics penetrable by air, in particular of a wire or felt, in which the fabric penetrable by air such as the wire is arranged to run over at least one roll whereby the movement of the fabric produces a positive pressure at an inlet side of the web or fabric in an inlet nip formed between the fabric and a face of the roll, and a negative pressure at an outlet side of the fabric or web in an outlet nip between the fabric and the roll face, these positive and negative pressures depending up on the permeability of the fabric penetrable by air.

Measurement of air penetrability (referred to as "permeability" below) of various fabrics penetrable by air is relevant to, e.g., the case of drying fabrics of a paper machine or filters, e.g., in connection with the monitoring of the condition thereof. Such measurements of permeability must be carried out in an industrial environment on the site. Permeability meters are included, e.g., in the standard equipment of each paper mill, and are used in particular in measurements of the permeability of plastic wires.

Plastic wires tend to become blocked by dust or as a result of mangling phenomenon as the wire mesh becomes smaller, which reduces the permeability thereof. A certain permeability is, however, highly important for the operation of the fabrics, e.g. in the case of the drying wires of a paper machine in view of the operation of the pocket ventilation means. On the basis of the measurements of permeability, it is decided whether, e.g., the wire of a paper machine or the filter fabric in a filter device must be replaced or cleansed.

Measurement of permeability may also be used to monitor or to control operation of various devices, for the cleaning or washing of fabrics. For example, in the case of wires, it is possible to judge from measurements of permeability, the condition of a wire at each particular time, so that the wire can be replaced when necessary before it is broken.

It has been a drawback of all of the prior-art methods and devices in the measurement of the permeability of wires, that it has been necessary to stop the paper machine for the time of the measurement of permeability. This is why the measurement has caused highly considerable costs, for the standstill time of a paper machine is highly expensive.

SUMMARY OF THE INVENTION

Accordingly, it is an object of the present invention to provide a method and a device for the measurement of the air penetrability of fabrics penetrable by air, in particular of a wire or felt, in a paper machine.

It is a more specific object of the present invention to provide a method and a device that are easier to operate, quicker, and more accurate than prior art methods and devices that perform corresponding measurement and that are, moreover, well suited for measurement of the permeability of fabrics placed in their operating position, especially of wire, without stopping the paper machine.

These and other objects are attained by the present invention which is directed to a method for measuring air penetrability or permeability of fabric in a paper machine, in which the fabric such as a wire or felt passes over at least one roll with a positive pressure formed in an inlet nip between a face of the roll and the moving fabric at an inlet side of the roll and a negative pressure formed in an outlet nip between the moving fabric and the roll face at an outlet side of the roll. The positive and negative pressures depend upon the permeability or penetrability of the fabric.

The method comprises the steps of mounting at least one device adjacent the fabric and roll and which is sealed with respect to the moving face so that an at least partially closed pressure space is formed between the device, the roll face, and the fabric, measuring pressure out of the pressure space while the fabric moves to thereby obtain a measured pressure value, and calculating the permeability or penetrability of the fabric from the measured pressure value.

The present invention is also directed to a device for measuring air penetrability or permeability of fabric such as a wire or felt in a paper machine, in which the fabric is arranged to run over at least one roll whereby movement of the fabric produces a positive pressure at an inlet side of the roll and in an inlet nip formed between the fabric and a roll face, and a negative pressure at an outlet side of the roll and in an outlet nip formed between the roll face and fabric. These positive and negative pressures depend upon the permeability or penetrability of the faric to air.

More specifically, the device comprises a plate, beam, or box mounted proximate to the moving fabric, extending substantially over the transverse width of the fabric, and being sealed with respect to the face of the roll to define, together with the roll face and the fabric, an at least partially closed pressure space. At least one measurement detector is provided at or in the pressure space for measuring the pressure. Additionally, means for determining the permeability or penetrability of the moving fabric based on the measured pressure, may be provided.

With a view to achieving the objects noted above and those which will become apparent below, the method of the present invention is characterized in that at least one device is mounted below the fabric penetrable by air such as a wire, the device being sealed relative to the moving roll face so that an at least partially closed pressure space is formed between the device, the roll face, and the fabric, where the pressure is measured out of the pressure space while the fabric penetrable by air such as a wire moves, and the permeability of the fabric penetrable by air is calculated from the measured pressure value.

On the other hand, the device in accordance with the present invention is characterized in that it comprises a plate, beam, box or equivalent which is mounted at the proximity of the moving fabric, extends substantially over the width of the fabric, and which is sealed relative to the moving roll face so that the device, the roll face, and the fabric penetrable by air together define an at least partially closed pressure space which is provided with at least one measurement detector for the measurement of the pressure, as well as means for detecting the measured pressure values for the determination of the permeability of the moving fabric.

Several remarkable advantages are achieved over prior art solutions by means of the present invention. Of these advantages, the following, e.g., should be noted. By means of the method and the device of the present invention, measurement of permeability can be carried out on fabrics such as wires placed in operating position without stopping the paper machine. The measurement of permeability can be carried out continuously, i.e. the condition of the wire can be monitored constantly. The measurement can be carried out as block measurement so that the measurement results are received from several different locations in the direction of width of the wire. On the basis of the measurement results obtained, a wire which is in inferior condition can be replaced before it is broken, in which case only replacement of the wire necessitates stopping of the paper machine. The other advantages and characteristic features of the present invention will become apparent from the following detailed description thereof.

BRIEF DESCRIPTION OF THE DRAWINGS

The present invention will be described in greater detail below with reference to the accompanying figures to which the present invention is, however, not to be strictly confined. In the drawings.

DESCRIPTION OF THE PREFERRED EMBODIMENTS

Figure 1:
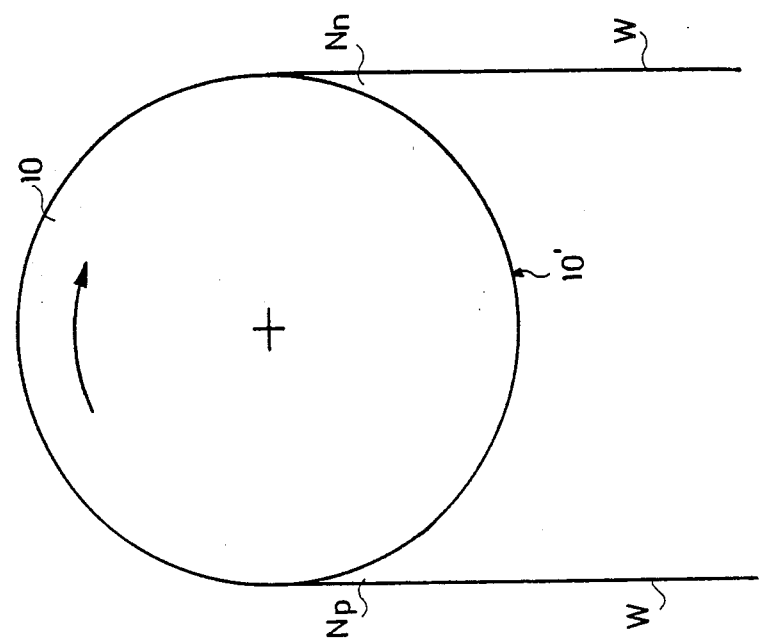
FIG. 1 is a schematic side view of a wire passing over a tension roll.

FIG. 1 thus illustrates a wire W which is passed over a roll 10 which is a tension roll in the embodiment illustrated therein. When the wire W runs over the roll 10, a positive pressure is formed at an inlet side of the wire in a "nip" $N_p$ between the wire W and the roll face 10' and, in a corresponding way, at an outlet side of the wire a negative pressure is formed in a nip $N_n$ between the wire W and the roll face 10'. The nip $N_p$ at the inlet side will be termed the positive nip and the nip $N_n$ at the outlet side will be termed the negative nip below.

When the permeability of the wire W becomes lower, i.e. when the wire is being blocked, the positive pressure in the positive nip $N_p$ is increased and correspondingly the negative pressure in the negative nip $N_n$ is increased. When the permeability of the wire W is high, i.e. when penetrability by air is good, then the positive pressure in the positive nip $N_p$ is lower and correspondingly the negative pressure in the negative nip $N_n$ is lower.

Under these circumstances, the permeability of the wire W could be measured, in principle, e.g., by means of the absolute values of the differences in pressure. In this connection it should, however, be emphasized that the differences in pressure are very strongly dependent upon the speed of the wire W. However, in a determination of the permeability, the speeds could be readily taken into account in the calculation formulae, so that it would be possible to determine the permeability along this route.

In experiments that were carried out, the differences in pressure that were obtained as a function of permeability were, however, so little and vague that it was impossible to determine the correlation on their basis between differences in pressure and permeability with sufficient accuracy. At the side of the positive pressure, i.e. in the positive nip $N_p$, the phenomena seemed to be carried into effect even if the differences in permeability between the wires tested were quite low (permeability $\omega \approx 710$ to $1370$ m$^3$/hm$^2$). Furthermore, it should be emphasized that it is quite difficult to carry out the measurement of pressure out of the nip itself.

Figure 2:
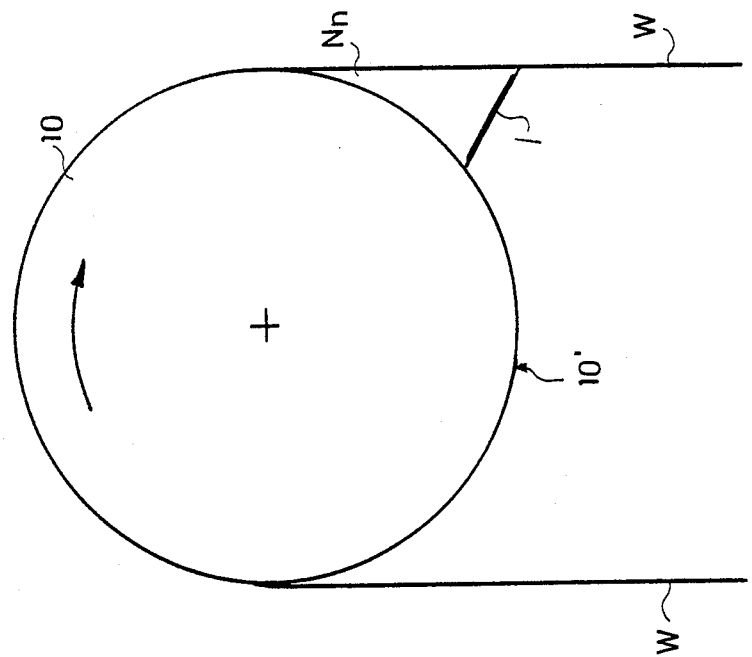
FIG. 2 is a view corresponding to FIG. 1, in which an obstacle plate is provided at an outlet side of the wire from the roll in a nip formed between the wire and the tension roll, for the purpose of pressure measurement.

When the above experiments were continued at the test plant, the negative nip $N_n$ between the wire W and the roll face 10' was provided with an obstacle plate 1, which is illustrated schematically in FIG. 2. As is shown in FIG. 2, the obstacle plate 1 was sealed both against the face 10' of the tension roll and against the wire W. When the run of the wire W was started, a clear increase in the level of negative pressure in the negative nip $N_n$ was noticed. In an exactly corresponding manner, it is already known from earlier UnoRun tests that the nip pressures are increased when the nip is provided with a UR tube and when the supply of air is, at the same time, closed.

Figure 3:
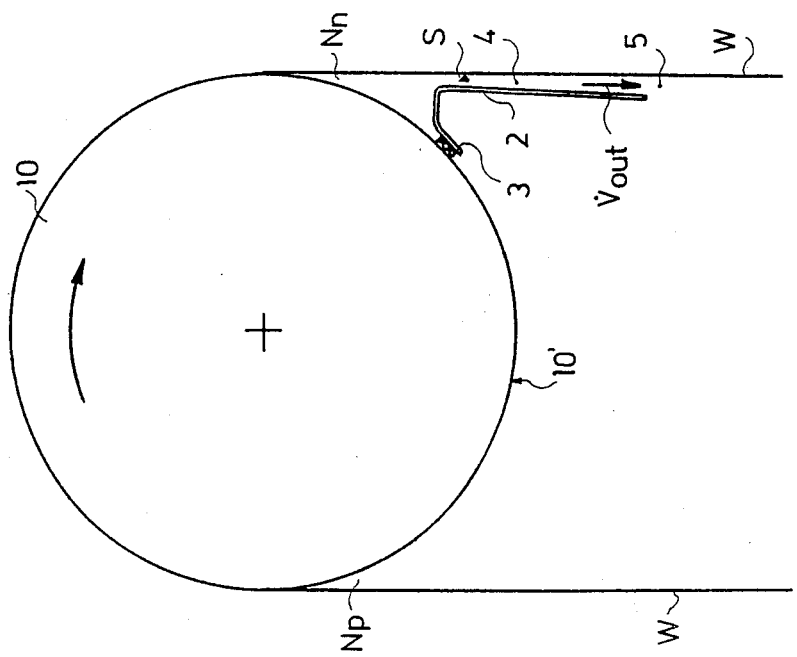
FIG. 3 is a view corresponding to FIG. 1, in which a particular measurement beam is provided at the outlet side of the wire with respect to the roll in a location corresponding to the plate location of FIG. 2.

When the invention was further developed, the following solutions were reached, of which the arrangement illustrated in FIG. 3 will first be examined and which is meant for the measurement of negative pressure. FIG. 3 illustrates the wire W which is arranged to run over the roll 10. The roll 10 may be any wire guide roll whatsoever, preferably a stationary guide roll. At the outlet side of the wire W with respect to the roll 10, in connection with the negative nip $N_n$, a measurement beam 2 or measurement box is provided in accordance with FIG. 3, which is sealed by means of a seal 3 relative to the roll face 10'. The measurement beam 2 is arranged in such a manner relative to the wire W that a gap S remains between the measurement beam 2 and the wire W, such gap S becoming larger in the direction of running of the wire W so that the gap S is "ejector-shaped".

The formation of negative pressure underneath the measurement beam 2 is thus based on an ejection effect of the wire W and the measurement beam 2. The measurement beam 2 is provided with pressure measurement detectors which are favorably conventional detectors of the pitot tube type. From underneath the measurement beam 2 at the middle of the gap S denoted with reference numeral 4 in FIG. 3, the average negative pressure p$_{stat}$ is measured, and from the outlet opening 5 of the gap the dynamic pressure p$_{dyn}$ is measured. The construction of the measurement detectors and the principle of measurement are described in more detail in connection with FIGS. 5 to 7.

The permeability of the wire can be concluded on the basis of the measurement results by examining the values of the dynamic pressure p$_{dyn}$, for it is fully certain that more open wires yield higher values of dynamic pressure p$_{dyn}$. Determination of blocking of the wire can be carried out, e.g., in the following ways.

A simple method is to run the characteristic curve of the wire when the wire is new, i.e. to measure the pressure values from a new wire. The measurement obtained can then be used as a "key" and compared with the measurement results obtained from a used wire. In this way it is possible to study the blocking of the wire as a function of time. However, it is a drawback of such a method that the pressures are clearly dependent on the running speed of the wire so that if the wire is run at several different speeds in operation, a fully reliable picture of the blocking of the wire cannot be obtained by means of this method.

Now, the permeability of the wire can be determined in the following manner. The magnitude of the gap S as well as the width L of the measurement beam or of a part of the same are known quantities. When the dynamic pressure p$_{dyn}$ is measured, the quantity of air ejected through the wire can be calculated by means of the following formula:

$$\dot{V}_u = 1.414 \cdot \sqrt{\Delta p_{dyn}} \cdot (\sqrt{l})^{-1} \cdot S \cdot L \ (m^3/s),$$

wherein
$\dot{V}_u$ = quantity of air ejected (m$^3$/s)
$\Delta p_{dyn}$ = dynamic pressure (Pa)
$\rho$ = density of air (kg/m$^3$)
S = gap (m)
L = width of gap (m)

EXAMPLE $\Delta p_{dyn}$ = 50 Pa
$\rho$ = 0.96 kg/m$^3$
S = 0.02 m
L = 0.5 m

When these values are placed in the above formula, the result is $\dot{V}_u = 0.102 \ m^3/s \ (= 367 \ m^3/h)$.

On the other hand, it is possible to measure from underneath the measurement beam 2 the total negative pressure which may be, e.g., of the order of 50 Pa. Thus, this value now corresponds to the "suction flow" which is the above 367 m$^3$/h. If the height H of the measurement beam is, e.g., 0.8 m, then the suction flow has taken place through the area 0.8×0.5=0.4 m$^2$. The suction flow per area there is:

$\dot{V}_u/A = 367/0.4 = 917.5 \ m^3/hm^2$.

The permeability can now be calculated in the normal manner as follows:

$$\omega = 917.5 \frac{\sqrt{100}}{\sqrt{50}} = 1297 \ m^3/hm^2.$$

If the method described above cannot be made to operate reliably, then the permeability of the wire W can be studied by following the outgoing quantity of air $\dot{V}_{out}$. For example, when the drying wire is blocked, i.e. when the permeability is reduced, the outgoing air quantity is reduced.

Figure 4:
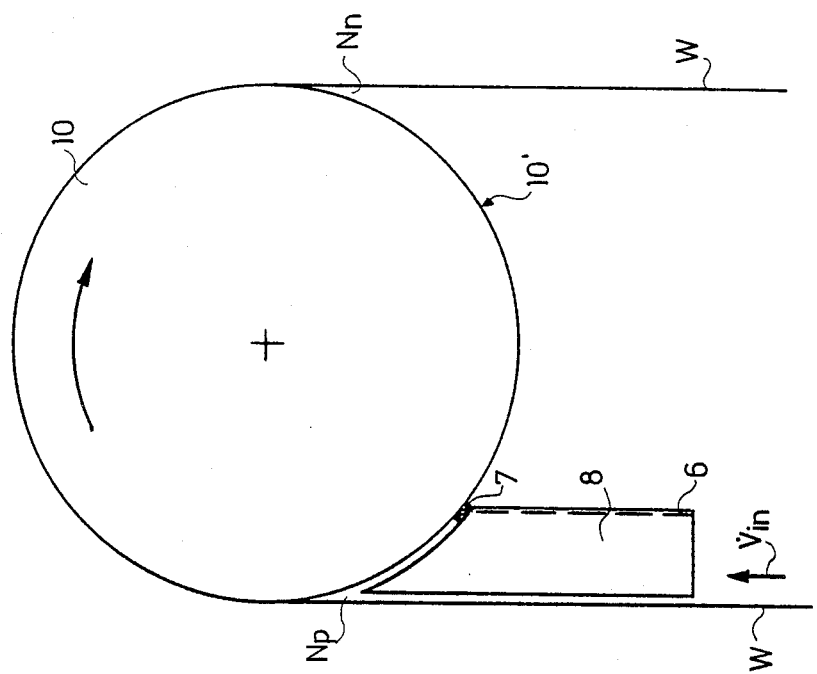
FIG. 4 is a view corresponding to FIG. 1 in which a measurement beam or box is provided at an inlet side of the wire with respect to the roll, in a nip formed between the wire and the tension roll.

From the side of positive pressure, the measurement can be carried out, in principle, in the corresponding manner and attempts have been made to illustrate the same in FIG. 4. Thus, in this embodiment in connection with the positive nip N$_p$, a measurement beam 6 (or measurement box) has been formed and which is sealed by means of a seal 7 relative to the roll face 10'. In the manner described above, the positive pressure or static positive pressure p$_{stat}$ can be measured there from underneath the measurement beam 6, e.g., from a measurement point 8 situated at the middle of the measurement beam 6 ($\dot{V}_{in}$ is the incoming quantity of air). The measurement results thereupon obtained can be compared with the "characteristic curve" of the wire W which has been determined from the new wire. Thus, the permeability values can be determined from the side of positive pressure in a manner corresponding to the manner described with relation to the preceding embodiment.

In order to improve the accuracy of the measurement results, the measurements can naturally be carried out from both the side of negative pressure and the side of positive pressure while drawing the necessary conclusions on the basis of the measurement results obtained. With such a joint measurement, the reliability and accuracy of the measurement results are naturally better than with measurement from one side only. In the drying section of a paper machine, the upper wire and lower wire must be separately measured because they are somewhat differently blocked, and such wires must be replaced at different times. The service life of the best wires is, as a rule, about 1 years, with it taking several months to result in a blocking of a wire so that it must be replaced, in all cases.

Figure 6:
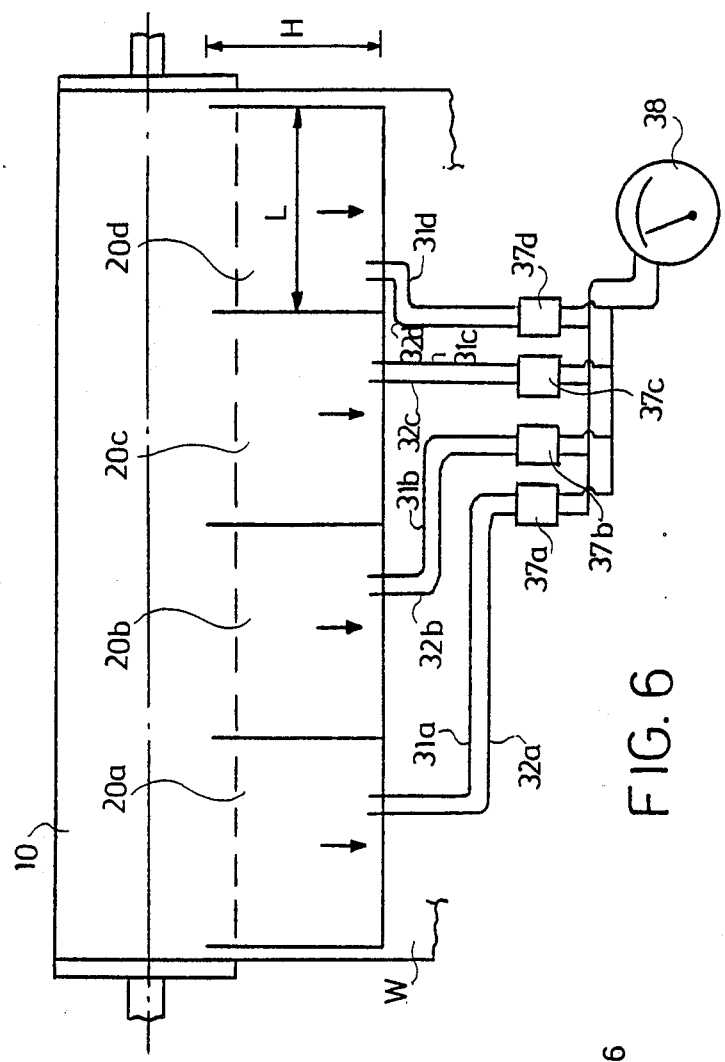
FIG. 6 is a view as seen from the left in FIG. 5.
Figure 5:
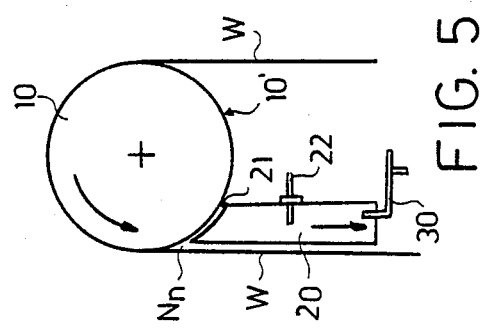
FIG. 5 is a schematic side view illustrating principles of measurement in accordance with the present invention.

The principles of the measurement arrangement and of the measurement method are described in more detail in connection with FIGS. 5 to 7. FIGS. 5 and 6 illustrate, e.g., a drying wire W which is passed over a wire guide roll 10. At the outlet side of the wire W in connection with the negative nip N$_n$, a measurement box 20 is installed which is, in the manner described above, sealed relative to the roll face 10' by means of a seal 21. In the direction of width of the roll 10, the measurement box 20 has been divided into several measurement blocks 20a ... 20d, the number thereof being shown to be four in the embodiment of FIG. 6. The number of such measurement blocks may naturally vary in accordance with the number of points in the direction of width of the wire W at which the measurements are intended to be carried out.

The principle of block measurement can be applied to all of the measurement arrangements described above, whereby both the obstacle plate 1 shown in FIG. 2 and the measurement beams 2 and 6 illustrated in FIGS. 3 and 4 may be divided into blocks in a corresponding manner. For the measurement of pressures, the measurement box 20 is provided with measurement detectors 22, 30 which are preferably pitot tubes used in prior art standard measurements. The embodiment shown in FIG. 5 is provided with two measurement detectors, of which the first measurement detector 22 which measures from below the measurement box 20 measures the static pressure $p_{stat}$ and the second measurement detector 30 which is fitted at the mouth of the measurement box 20 measures the dynamic pressure $p_{dyn}$.

If the permeability of the wire is determined exclusively by examination of the values of static pressure, then a second measurement detector 30 is naturally not needed. In a corresponding manner, if the determinations of permeability are carried out by means of dynamic pressures or differences in pressure, then the first measurement detector 22 illustrated in the figure is not needed because the construction of the second measurement detector 30 is such that both the static pressure $p_{stat}$ in the measurement box 20 and the dynamic pressure $p_{dyn}$ can be determined by means thereof.

Figure 7:
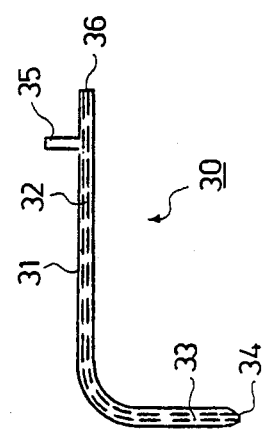
FIG. 7 is a schematic illustration of construction of a measurement detector used in the measurement of the present invention.

The construction of the second measurement detector 30 is illustrated in greater detail in FIG. 7. Thus, the second measurement detector 30 comprises a detector of the pitot tube type, in which two tubes situated one inside the other are utilized. The outer tube 31 is used for the measurement of the static pressure $p_{stat}$, and for this purpose is provided with an outlet 35 for the static pressure $p_{stat}$ from which the detector data are transmitted further along measurement ducts, e.g. to a pressure gauge or equivalent. One end of the outer tube 31 is closed, and holes 33 have been instead made into the tube some distance from the end of the tube, through which the static pressure prevailing in the measurement box 20 can be measured.

On the contrary, the inner tube 32 is intended for the measurement of the total pressure $p_{tot}$ and is provided with an outlet 36 for the total pressure $p_{tot}$. The inner tube 32 is opened into an opening 34 provided at the end of the measurement detector 30. The dynamic pressure there $p_{dyn}$ is the difference between the total pressure $p_{tot}$ and the static pressure $p_{stat}$, i.e. of the difference in pressure, so that $$p_{dyn} = p_{tot} - p_{stat}.$$

FIG. 6 is a schematic illustration of an arrangement of the block measurement principle. As illustrated in FIG. 6, the measurement box 20 has been divided into several measurement blocks $20a \ldots 20d$ in the direction of width of the web W, the number of such blocks being illustrated as four in the embodiment shown in this figure. The number of blocks may however differ from that shown in the embodiment of this figure. The width of the blocks is denoted by L, and the height of the measurement box 20 by H.

The embodiment illustrated in FIG. 6 is equipped for the measurement of the dynamic pressure and therefore each measurement block $20a \ldots 20d$ is provided with measurement detectors both for the measurement of the static pressure and for the measurement of the total pressure. Thus, the measurement detectors in each measurement block are connected to first measurement ducts $31a \ldots 31d$ on the one hand, which are measurement ducts for the static pressure, and to second measurement ducts $32a \ldots 32d$ on the other hand, which are measurement ducts for the total pressure. Such measurement ducts are passed through selector valves $37a \ldots 37d$ to a pressure gauge 38 or equivalent from which, depending upon the position of the selector valves $37a \ldots 37d$, it is possible to read the total pressure $p_{tot}$, the static pressure $p_{stat}$, or the difference in pressure between the total pressure and the static pressure, i.e. the dynamic pressure $p_{dyn}$, with respect to each measurement block $20a \ldots 20d$.

The measurement arrangement may naturally also differ from the embodiment illustrated in FIG. 6. One possible alternative is such that the measurement ducts in each measurement block $20a \ldots 20d$ are connected to a pressure gauge or equivalent of their own, in which case the values of each measurement block can be read at the same time. Additionally, instead of being connected to a pressure gauge, the measurement ducts may be connected to a calculator device such as a microcomputer or equivalent which is programmed so that it yields the permeability values of the wire directly instead of pressure readings. If the condition of the wire is determined exclusively by examination of the values of static pressure, only the measurement detector 22 for static pressure is naturally needed in each measurement block $20a \ldots 20d$ from which, unlike the embodiment of FIG. 6, only one duct is passed to the calculator, to the pressure gauge, or equivalent.

The preceding description of the present invention is merely exemplary, and is not intended to limit the scope thereof in any way. Various details of the present invention may vary within the scope of the inventive concepts and may differ from the details given above which have been presented for the sake of example only.

What is claimed is:

1. Method for measuring air penetrability or permeability of fabric in a paper machine, in which the fabric passes over at least one roll with a positive pressure formed in an inlet nip between a face of the roll and the moving fabric at an inlet side of the roll and a negative pressure formed in an outlet nip between the moving fabric and the roll face at an outlet side of the roll, the positive and negative pressures depending upon the permeability or penetrability of the fabric, comprising the steps of mounting at least one device adjacent the fabric and roll and which is sealed with respect to the moving roll face so that an at least partially closed pressure space is formed between said device, the roll face and the fabric, measuring pressure out of said pressure space while the fabric moves, to thereby obtain a measured pressure value, and calculating the permeability or penetrability of the fabric from the measured pressure value.

2. The method of claim 1, wherein said at least one device is mounted at the outlet side of the roll with respect to the moving fabric, so that the permeability or penetrability of the moving fabric is determined on the basis of the negative pressure that is measured.

3. The method of claim 1, wherein said at least one device is mounted at the inlet side of the roll with respect to the moving fabric, so that the permeability or penetrability of the moving fabric is determined on the basis of the positive pressure that is measured.

4. The method of claim 1, comprising a plurality of devices, with at least one of said devices mounted at the inlet side and at least one of said devices mounted at the outlet side of the roll with respect to the moving fabric, whereby the permeability or penetrability of the fabric is determined on the basis of both the positive and negative pressures that are measured.

5. The method of claim 1, comprising the additional step of carrying out measurements of pressure at several points along a transverse direction with respect to the moving fabric.

6. The method of claim 1, wherein said device is also sealed with respect to the moving fabric and static pressure is measured out of the pressure space that is formed.

7. The method of claim 1, wherein said at least one device is mounted to leave a gap between the same and the moving fabric, whereby dynamic pressure of air flowing in the gap in a direction of movement of the fabric, is measured.

8. The method of claim 1 wherein said fabric is a wire or a felt.

9. In a paper machine, a device for measuring air penetrability or permeability of fabric in the paper machine, in which the fabric is arranged to run over at least one roll whereby movement of the fabric produces a positive pressure at an inlet side of the roll and in an inlet nip formed between the fabric and a roll face and a negative pressure at an outlet side of the roll and in an outlet nip formed between the roll face and fabric, these positive and negative pressures depending upon the permeability or penetrability of the fabric, comprising a plate, beam or box mounted proximate to the moving fabric, extending substantially over the transverse width of the fabric, and being sealed with respect to the face of the roll to define, together with the roll face and the fabric, an at least partially closed pressure space, and at least one measurement detector provided at or in said pressure space for measuring the pressure.

10. The combination of claim 9, additionally comprising means for determining the permeability or penetrability of the moving fabric based on the measured pressure.

11. The combination of claim 10, wherein said plate, beam, or box is mounted at the outlet side with respect to the roll, so that said pressure space formed comprises a zone of negative pressure.

12. The combination of claim 10, wherein said plate, beam, or box is mounted at the inlet side with respect to the roll, so that said pressure space formed comprises a zone of positive pressure.

13. The combination of claim 10, wherein any combination of plates, beams, or boxes is mounted both at the inlet side and at the outlet side of the roll, to define pressure spaces each comprising a zone of negative pressure or a zone of positive pressure.

14. The combination of claim 10, wherein said plate, beam, or box is divided into several measurement blocks, and additionally comprising at least one measurement detector provided for each said block.

15. The combination of claim 10, wherein said pressure space is additionally sealed with respect to the moving fabric, and said measurement detector is disposed to detect static pressure prevailing in said pressure space.

16. The combination of claim 10 wherein said plate, beam or box is mounted to define a gap between the same and the moving fabric.

17. The combination of claim 16, wherein said measurement detector is disposed in said gap to measure static pressure in said pressure space.

18. The combination of claim 16, wherein said measurement detector is fitted at a mouth or said gap to measure dynamic pressure of air flowing through said gap.

19. The combination of claim 10, wherein said measurement detector comprises two tubes, one inside the other, with an outer one of said tubes provided with an outlet for static pressure and an end of said outer tube being closed with holes being situated in the outer tube at a distance away from the end of said tube, and an inner one of said tubes provided with an outlet at one end thereof for total pressure and another opening provided at an opposite end thereof, whereby dynamic pressure is calculated as a difference between the total pressure and the static pressure.

20. The combination of claim 9, wherein said fabric is a wire or a felt.

* * * * *